UNITED STATES PATENT OFFICE.

HENRI CHAUMAT, OF PARIS, FRANCE.

PREPARATION OF THE INDIGO-VAT EMPLOYED IN DYEING.

No. 12,946. Specification of Reissued Letters Patent. Reissued April 27, 1909.

Original No. 885,978, dated April 28, 1908, Serial No. 389,460. Application for reissue filed October 8, 1908. Serial No. 456,848.

*To all whom it may concern:*

Be it known that I, HENRI CHAUMAT, a citizen of the Republic of France, and resident of Paris, France, have invented a new and useful Preparation of the Indigo-Vat Employed in Dyeing, which improvement is fully set forth in the following specification.

As is known in dyeing the name of "vat" is generally given to the bath in which the indigo is dissolved. The indigo vat has heretofore been prepared either by fermentation or by means of chemical products.

The present invention has for its object an electrolytic process whereby an indigo vat suitable for dyeing may be speedily obtained.

This process consists broadly in treating with an electric current, while protected from the air, a bath of alkaline or alkaline earthy salts, such as:—carbonates, sulfites, busulfites or sulfids, employed either alone or in the state of mixture and in particular, carbonate of soda. The anode at which the current enters the bath is constituted by carbon or a metal which is not oxidizable under the conditions of the operation. The cathode is formed in the manner hereinafter described, from a special mixture.

In order to form the cathode powdered indigo blue is taken. As in the fermentation processes this powder should be reduced to an impalpable state. This indigotin powder is mixed intimately with powdered graphite or a metallic powder which is a conductor of electricity, and by any appropriate means, such as molding or otherwise, a cathode is produced the form of which will depend upon the form and dimensions of the vat employed. For example, as an industrial process the mixture of conducting powder and indigotin powder may be packed in a bag around a metallic or carbon conducting core. The two powders might likewise be agglomerated by any suitable substance.

The bath of alkaline or alkaline earthy salts, such as carbonate of soda for example, being placed in an appropriate vat, there is arranged above the level of the liquid, with a view to preventing any contact with the atmosphere, either a stratum of an insulating liquid such as oil, or an insulating atmosphere, such as carbonic acid. The anode and the cathode described above should be introduced into the bath before this takes place. The anode may be placed inside a diaphragm.

Under the influence of the electric current oxygen is produced at the anode and this should be disposed of in any convenient manner, for example, by suction in the chamber formed by the diaphragm around the anode; if the bath contains sulfids or sulfites the diaphragm is not necessary as the oxygen is absorbed by the bath. On the cathode, on the other hand, hydrogen is formed; this reduces the indigotin and transforms this insoluble indigotin into indigo white soluble in alkali which is produced at the cathode in exactly the proper quantity for dissolving the indigo white. In proportion as the indigo white is dissolved in the alkaline solution of the bath, which solution is more or less caustic, there forms in the chamber constituted by the diaphragm around the cathode, conducting powder which is disaggregated from this cathode. This conducting powder is subsequently removed and in any case does not enter the vat which contains the liquid really utilizable for the indigo vat. In this manner a solution of indigo white in the more or less caustic alkaline salts of the bath is thus obtained very speedily, the proportion being very high. The liquid thus obtained may be prepared on the spot and be used at once for dyeing; or it may be drawn off protected from the air and preserved indefinitely in receptacles which are either soldered or closed in any other hermetic manner.

The importance of this novel process will therefore be understood as it permits of preparing in advance and in very large quantities the liquids required for the formation of the indigo vat. Again, generally speaking, among the numerous advantages presented by the process forming the object of the present invention, the following may be cited:—1. This process permits of forming an indigo vat in a few hours while the fermentation processes hitherto employed necessitate a very long time and constitute excessively delicate operations calling for careful surveillance. 2. By this process solutions are obtained which contain absolutely nothing but indigo white and the quantities of more or less caustic alkaline salts necessary for dissolving this indigo white. 3. Far more concentrated solutions are obtained than by what are termed the fermentation processes. 4. It is possible to preserve the indigo solution indefinitely in a closed vessel and consequently to place this solution on the market for use in dyeing. 5. The bath obtained is perfectly homogeneous and its employment in dyeing piece goods accordingly gives excellent results as regards the uniformity of the shade obtained. 6. It is very economical. 7. The bath does not contain any foreign body and consequently gives a remarkable richness of tone.

Having thus described my invention what I claim is:—

1. An electrolytic process for the preparation of the indigo vat employed in dyeing, consisting in treating by the electric current, with exclusion of air, a solution of alkaline salts, placing an anode in a chamber separated from the bath by a diaphragm, said anode being constituted by a conducting body which is not oxidizable in the conditions of the operation, forming a cathode by a mixture of a powder which is a conductor of electricity and powder of indigo, and protecting the vat from external oxidation.

2. An electrolytic process for the preparation of the indigo vat employed in dyeing, consisting in treating by the electric current, with exclusion of air, a solution of earthy-alkaline salts, placing an anode in a chamber separated from the bath by a diaphragm, said anode being constituted by a conducting body which is not oxidizable in the conditions of the operation, forming a cathode by a mixture of a powder which is a conductor of electricity and a powder of indigo, and protecting the vat from external oxidation.

3. An electrolytic process for the preparation of the indigo vat employed in dyeing, consisting in treating by the electric current, with exclusion of air, a solution of alkaline sulfids; the anode being constituted by a conducting body which is not oxidizable in the conditions of the operation and the cathode being formed by a mixture of powder which is a conductor of electricity and powder of indigo, and protecting the vat from external oxidation.

In testimony whereof I have signed this specification in the presence of two subscribing witnesses.

HENRI CHAUMAT.

Witnesses:

LÉON CHARLES LOISEL,
GEORGES CARRIÉRE.